United States Patent [19]

Villasuso

[11] Patent Number: 5,257,973
[45] Date of Patent: Nov. 2, 1993

[54] SEALING SLEEVE AND METHOD FOR LAPAROSCOPY

[76] Inventor: Raul Villasuso, 675 W. North Ave., Suite 201, Melrose Pk., Ill. 60160

[21] Appl. No.: 831,406

[22] Filed: Feb. 5, 1992

[51] Int. Cl.⁵ ............................................. A61M 5/32
[52] U.S. Cl. .................................. 604/49; 604/175; 604/177; 128/DIG. 26; 128/912
[58] Field of Search ............... 604/174, 175, 177, 178, 604/49; 128/DIG. 6, DIG. 26, 912

[56] References Cited

U.S. PATENT DOCUMENTS

| | | | |
|---|---|---|---|
| 3,253,594 | 5/1966 | Matthews et al. | 128/DIG. 26 X |
| 3,663,965 | 5/1972 | Lee, Jr. et al. | 604/175 X |
| 3,817,251 | 6/1974 | Hasson . | |
| 4,315,513 | 2/1982 | Nawash et al. | 604/175 X |
| 4,488,877 | 12/1984 | Klein et al. | 604/175 |
| 4,533,349 | 8/1985 | Bark | 604/174 |
| 4,578,063 | 3/1986 | Inman et al. | 604/175 |
| 4,583,977 | 4/1986 | Shishov et al. | 604/174 |
| 4,597,756 | 7/1986 | Raible | 604/175 |
| 4,617,933 | 10/1986 | Hasson . | |
| 4,645,492 | 2/1987 | Weeks | 604/174 |
| 4,645,504 | 2/1987 | Byers | 604/175 X |
| 4,650,473 | 3/1987 | Bartholomew et al. | 604/174 |
| 4,668,222 | 5/1987 | Poirier | 604/175 |
| 4,944,732 | 7/1990 | Russo | 604/175 X |
| 4,985,033 | 1/1991 | Boebel et al. | 604/174 X |
| 5,002,557 | 3/1991 | Hasson | 604/174 X |
| 5,092,849 | 3/1992 | Sampson | 604/175 |

FOREIGN PATENT DOCUMENTS 2019219 10/1979 United Kingdom .............. 604/174

Primary Examiner—Randall L. Green
Assistant Examiner—Mary Beth Jones
Attorney, Agent, or Firm—Welsh & Katz, Ltd.

[57] ABSTRACT

A sealing sleeve for use with a cannula in open laparoscopy is disclosed. The sleeve of the subject invention has a conical shaped collar defining a passageway for feeding the cannula therethrough. The collar is formed of a resilient medically inert material capable of conforming to the edges of an incision thereby forming a gas tight seal and maintaining the pneumoperitoneum during the laparoscopy. The sleeve also includes a polygonal tube connected to the collar and rigid supports attached to the polygonal tube for receiving a suture to maintain the cannula in place with respect to the patient.

7 Claims, 1 Drawing Sheet

SEALING SLEEVE AND METHOD FOR LAPAROSCOPY

BACKGROUND OF THE INVENTION

The present invention relates generally to cannulas for use in laparoscopic surgery and more particularly to a cannula which prevents the escape of gas from a body cavity in which a laparoscopic surgical procedure is being performed.

In performing laparoscopy surgery, an incision is made in a patient to admit a cannula which serves as a conduit for the introduction of minute surgical instruments into the peritoneal cavity. The peritoneal cavity is generally filled with gas to expand the surrounding tissue to create a suitably sized operating space.

During manipulation of the instruments in a surgical procedure, the pressurized integrity of the peritoneal cavity or pneumoperitoneum must be maintained. Therefore, it is necessary that there be a proper seal between the cannula and body tissue at the incision point. To attain this objective, prior art devices have typically employed a conical shaped sealing sleeve which generally is constructed using a rigid material. Upon insertion into the incision, the sleeve's conical geometry pushes or displaces outward the tissue surrounding the incision. The tissue's natural resiliency will then cause the tissue to try to return to the tissue's original position which creates a sealing force against the surface of the sealing sleeve.

However, if there is major movement of the cannula during an operation, the tissue's resiliency may be insufficient to supply an adequate sealing force against the rigid sleeve; therefore, prior devices attempt to maintain the integrity of the seal during the procedure through the use of positioning means so movement of the cannula and sealing sleeve relative to the patient's tissue is reduced. Two devices as disclosed in U.S. Pat. No. 3,817,251 and U.S. Pat. No. 4,985,033 employ hooks or clamps attached to the cannula and the use of sutures to tie these hooks or clamps to a patient's tissue. Another device as disclosed in U.S. Pat. No. 5,002,557 employs an inflatable membrane at the insertable end of the cannula and positions the cannula by capturing a patient's tissue between the sealing sleeve and the expanded membrane. The nature of the laparoscopic procedure however, can require significant reorientation of the cannula during surgery and these prior art devices only tend to minimize relative movement during unintentional reorientation.

Recognizing the possibility of a potentially hazardous loss of the gas tight seal from movement of the cannula or from an uneven sealing force if the shape of the incision does not correspond to the cross-sectional geometry of the sealing sleeve, surgeons typically insert and affix such prior art devices to the patient so there is a significant downward force exerted by the sealing collar on the tissue. Such downward force causes greater displacement of the tissue surrounding the incision thus increasing the range of movement of the sealing sleeve which may be compensated for by the resilient nature of the tissue. This downward force and resulting displacement in turn often results in localized trauma to the tissue. Movement of the cannula during the operation exerts additional force on portions of the incision which can also result in localized trauma.

SUMMARY OF THE INVENTION

A primary object of the present invention is, a novel sealing means for maintaining the pneumoperitoneum during open laparoscopic surgery, without relying primarily on the resiliency of the patient's body tissue.

Another object of the invention is to allow for a significant amount of reorientation of the cannula in its operative position while maintaining the integrity of the seal.

A further object of the present invention is a disposable sealing device for use in laparoscopy which allows the cannula to be reused.

A still further object of the present invention is to reduce the possibility of localized trauma in the use of a cannula during laparoscopy by reducing the force of the collar on the tissue surrounding the incision.

According to the present invention a sealing sleeve is used with a cannula for insertion into an incision in a patient's abdomen. The sealing sleeve includes a collar having a first portion and a second portion, with the first portion having a conical outer surface having circumferential ribs and diminishing in diameter from an upper end to a lower end, the outer surface being resilient and flexible for conformance to the contours of the skin surrounding the incision, the collar having an inner surface defining an axial passageway for acceptance of the cannula; a polygonal tube matingly engaged to the second portion of the collar; a plurality of ears, the ears being connected to the polygonal tube, with each ear having a notch and a slit for receiving a suture, thereby anchoring the sealing sleeve and cannula to the patient.

The collar's flexible outer surface conforms to the contours of the incision, therefore, the sealing sleeve will effect a gas-tight seal without significant downward force on the cannula, thus reducing the possibility of localized trauma.

Should a surgeon apply excessive downward force during insertion of the cannula, the outer surface of the collar will flex and absorb a portion of the force applied at the incision point. This absorption also reduces the possibility of localized trauma to the tissue surrounding the incision.

Further, the resilience of the collar's material allows significant movement and reorientation of the cannula while maintaining a suitable force on the patient's tissue. Consequently the gas-tight seal between the cannula and incision remains intact. Likewise, the flexibility of the collar's material will absorb a portion of localized forces caused by the reorientation. Consequently, the possibility of localized trauma to the tissue will be reduced.

Further objects, features and advantageous of the present invention will become apparent from the following detailed description when taken in conjunction with the accompanying drawings wherein like reference numerals designate like elements through the several views.

DETAILED DESCRIPTION OF THE INVENTION

Figure 1:
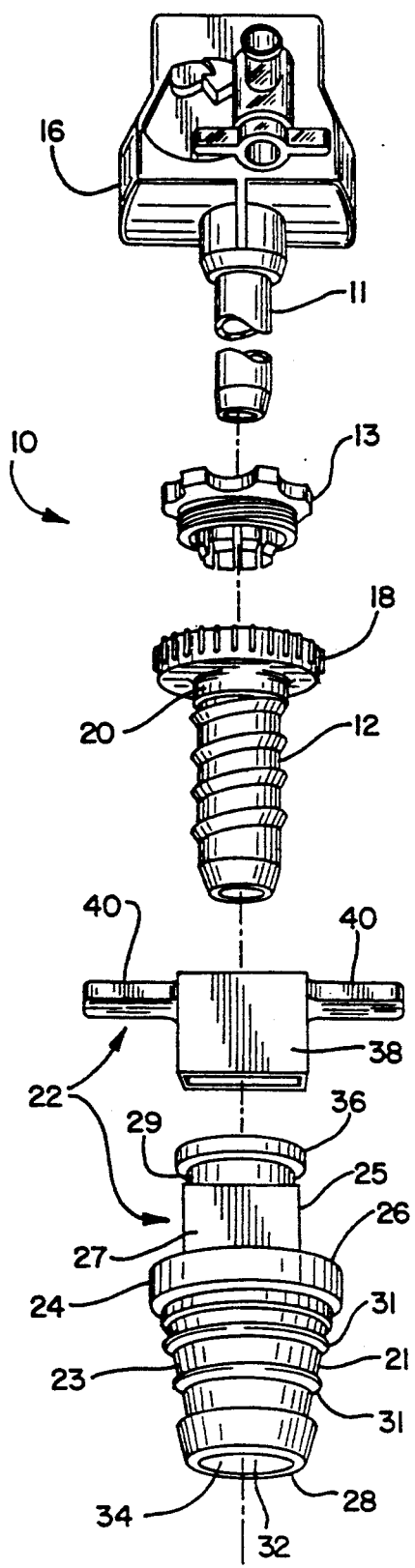
FIG. 1 is an exploded perspective view of the cannula and the sealing sleeve according to the present invention installed on a cannula.

Referring to FIG. 1, the cannula 10 therein shown includes a hollow shaft portion 11, a mounting cylinder 12, a placement locking ring 13 and gas valve means 16. The mounting cylinder 12 includes an annular positioning flange 18 extending radially outward from the upper end of the mounting cylinder. The positioning flange 18 includes a concentric protruding lip 20 (FIG. 2) axially aligned with the mounting cylinder 12 and disposed on the face of the positioning flange facing the lower end of the hollow shaft portion 11. The outer surface of the mounting cylinder 12 is threaded. The cannula is preferably made of rigid plastic such as high density polyethylene or the like, but may also be made of other materials such as stainless steel.

Figure 2:
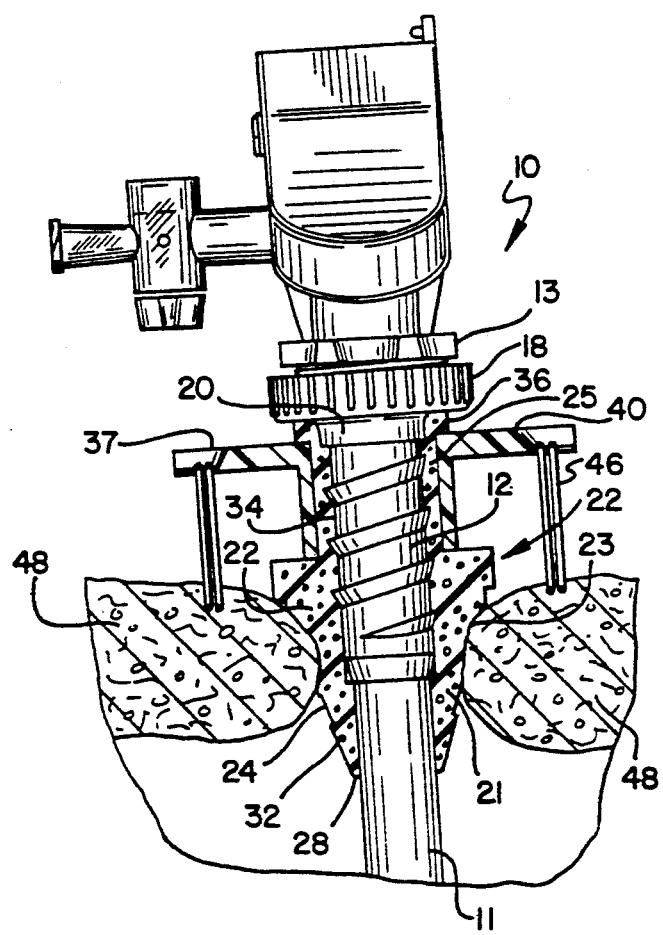
FIG. 2 is a partial sectional view of the sealing sleeve and cannula extended through body tissue and in a tilted operative position.

In FIG. 1, a preferred form of the sealing sleeve or device according to the present invention is shown at 22. The sealing sleeve 22 comprises a collar 24 with a first portion 21 having a flexible conical shaped outer surface 23 which diminishes in diameter from its upper end 26 to its lower end 28. The outer surface 23 includes at least one and preferably a plurality of ribs 31 extending circumferentially around the outer surface and axially spaced along its length. Integrally connected to and extending vertically from the upper end 26 of the first portion 21 is a second portion 25. The lower portion 27 of the second portion 25 has a polygonal outer periphery with the preferred embodiment having a square periphery, and the upper portion 29 of the second portion has a circular outer periphery. An annular sealing flange 36 is integrally connected to and extends radially outward from the upper end of the second portion 25. As seen in FIG. 2, a tubular inner surface 34 extends vertically through the first portion 21 and the second portion 25 of the collar 24. The tubular inner surface 34 of the collar 24 defines a passageway 32 for feeding the hollow shaft portion 11 and mounting cylinder 12 of the cannula 10 therethrough.

The tubular inner surface 34 of the collar 24 is threaded for threaded movement on the threads on the outer surface of the mounting cylinder 12. The diameter of the inner surface 34 and the outer diameter of the mounting cylinder 12 are sized so that upon screwing the sealing sleeve 22 onto the mounting cylinder 12, a gas tight seal is formed. In an alternate embodiment of the invention (not shown), the surface on the outer diameter of the mounting cylinder 12 is smooth. The inner surface 34 of the collar 24 also has a smooth surface and is sized to achieve a snug, friction fit with respect to the surface on the outer diameter of the mounting cylinder 12 as known in the art. Insertion of the mounting cylinder 12 through the passageway 32 will thereby create a gas tight seal.

Referring to FIG. 1, the sealing sleeve 22 also comprises a polygonal tube 38 having an inner surface matingly engaging the outer surface of the second portion 25 of the collar 24 between the upper end 26 of the first portion 21 and the sealing flange 36. The mating engagement between the polygonal tube 38 and lower portion 27 of the second portion 25 prevents rotational movement between the collar 24 and polygonal tube. The polygonal tube 38 includes an upper face 37 which abuts the sealing flange 36 and defines a hole 39 having a diameter greater than the outer diameter of the upper portion 29 of the second portion 25 but less than the outer diameter of the sealing flange thus preventing axial movement of the collar 24 relative to the polygonal tube. Preferably, the polygonal tube 38 is made of high impact plastic such as high density polyethylene or the like but may also be made of other materials such as aluminum or stainless steel.

Rigid supports 40 are integrally connected to the polygonal tube 38 for receiving a suture 46 (FIG. 2) to maintain the cannula 10 in place with respect to the patient. In the illustrated preferred embodiment the rigid supports 40 include two ears 42a and 42b extending outward from opposing sides of the polygonal tube 38. The ears 42a and 42b each include notches 44a and 44b respectively extending along the outer portion of their upper surfaces. As seen in FIG. 2, at the base of each of the notches 44a, 44b is a slit 45a and 45b for receiving and anchoring the sutures.

Figure 3:
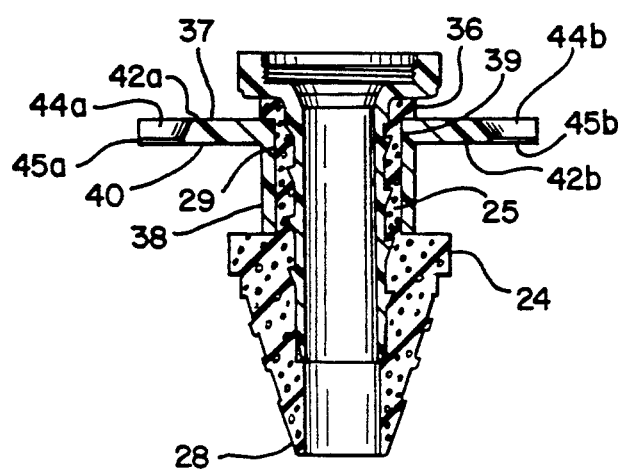
FIG. 3 is a sectional view of the sealing sleeve shown in FIG. 2.

In a laparascopic surgical procedure, the surgeon assembles the cannula 10 by positioning the mounting cylinder 12 on the hollow shaft portion 11 so the hollow shaft portion will extend the desired distance into the patient's peritoneal cavity. The placement locking ring 13 is then screwingly inserted into the upper face of the positioning flange 18 which thereby locks the mounting cylinder 12 onto the hollow shaft portion 11. The hollow shaft portion 11 is then inserted into the passageway 32 and the sealing device is slid up the hollow shaft portion. The sealing device 22 is then screwed onto the mounting cylinder 12 until the upper surface of the sealing flange 36 abuts the positioning flange 18 and the protruding lip 20 on the positioning flange displaces the sealing flange outward forming an elastomeric gas-tight seal (FIG. 3). The abutting relationship acts to properly position the sealing sleeve 22 on the cannula 10. As shown in FIG. 2, the hollow shaft portion 11, mounting cylinder 12, and attached sealing device 22 are then inserted into an incision which forms an opening into a patient's peritoneal cavity. Fascial sutures 46 which have been previously inserted into a patient's tissue 48 are then pulled upward and tied to the notches 44a, 44b and slits 45a, 45b on the ears 42a, 42b. This maneuver pulls the patient's tissue 48 firmly against the collar 24.

To maintain a proper seal between a patient's tissue 48 and the sealing sleeve 22 at the point of incision the present invention contemplates the collar 24 being composed of a resilient material having sufficient flexibility to allow the outer surface 23 to conform to the contours of the incision. Preferably the collar 24 is made of a medically inert, yet flexible polymeric material such as teflon, but may also be made of other materials such as medical grade silastic rubber. The illustrated preferred embodiment of the present invention contemplates the first portion 21 of the collar 24 being solid between the outer surface 23 and the tubular inner surface 34. It is also contemplated in an alternate embodiment of the invention (not shown), the outer surface 23 and inner tubular surface 34 define a hollow chamber.

As shown in FIG. 2, during insertion of the sealing sleeve into the incision, the conical geometry of the first portion 21 will displace the tissue 48 surrounding the incision outward. The natural resilience of the tissue 48 will supply a force against the flexible outer surface 23 of the first portion 21 and cause it to deform inward. Because of this deformation, the resilient material of the first portion 21 will cause the outer surface 23 to apply an opposing force against the tissue 48. The opposing forces between the tissue 48 and outer surface 23 will create the necessary gas-tight seal between the cannula 10 and the incision. The circumferential ribs 31 act to prevent the tissue 48 from sliding toward the lower end 28 of the first portion 21 which would reduce the displacement of the tissue and corresponding force between the outer surface 23 and the tissue.

Upon insertion of the cannula 10 and sealing sleeve 22 into the incision, the flexibility of the outer surface 23 of the first portion 21 allows the outer surface to conform to the shape of the incision. The surgeon will visually ascertain the conformance of the first portion 21 to the contours of the incision. Because of the ability of the outer surface 23 to conform, a gas tight seal can be effected without a substantial amount of downward force, thus reducing the traumatization of the tissue 48 surrounding the incision.

Should a surgeon apply excessive downward force during insertion of the cannula 10, the deformation of the outer surface 23 of the first portion 21 will increase and absorb a portion of the force applied at the incision point. Therefore, the possibility of localized trauma to the tissue 48 surrounding the incision is reduced.

As shown in FIG. 2, during the laparoscopic procedure, the surgeon will either purposely or inadvertently reorient the cannula 10. This reorientation of the cannula 10 will also cause the sealing device 22 to correspondingly tip in the same direction. The side of the first portion 21 opposite the direction in which the cannula 10 is being tipped will tend to pull away from the tissue 48. The resilience of the collar's material will allow the outer surface 23 of the first portion 21 to recover outward and maintain a suitable force on the patient's tissue 48. As a result, the gastight seal between the cannula and incision remains intact. Likewise, the side of the first portion 21 in the same direction in which the cannula 10 is being tipped will tend to be forced into the tissue 48. The flexibility of the outer surface 23 of the first portion 21, will allow the collar to absorb a portion of this force. As a result, the possibility of localized trauma to the tissue 48 will be reduced.

After the operation is completed, the surgeon will remove the cannula 10 and sealing sleeve 22 from the incision. The sealing sleeve 22 can be discarded and the cannula 10 can then be cleaned, sterilized and reused.

While a particular embodiment of the sealing sleeve for open laparoscopy has been shown and described, it will be appreciated by those skilled in the art that changes and modifications may be made thereto without departing from the invention in its broader aspects and as set forth in the following claims.

What is claimed is:

1. A sealing assembly for open laparoscopic surgery to provide a gas tight conduit into a peritoneal cavity by insertion through an incision in a patient's abdomen, the assembly comprising:
   a cannula having tubular means for the introduction of surgical instruments into the body; and
   a collar having a first portion having a generally conical outer surface extending from an upper end to a lower end, and an inner surface defining an axial passageway, said tubular means extending through said passageway, said tubular means and said passageway being configured to provide a fluid tight seal therebetween, said outer surface being inwardly deformable and resilient to conform to the contours of the skin surrounding the incision, whereby a fluid tight seal may be made by said first portion of said collar with said skin about said cannula, said collar further includes a second portion integrally connected to said first portion and extending vertically from said upper end of said first portion with said axial passageway extending vertically through said second portion, said second portion having a sealing flange located at an upper end of said second portion for forming a sealing engagement with a protruding lip on said cannula.

2. The device according to claim 1 further including rigid means engaging said collar for receiving at least one suture to maintain said cannula in place with respect to the patient.

3. The device according to claim 2 where said rigid means comprises a plurality of ears, each of said ears having notch means for receiving said at least one suture, said ears integrally connected to a tube which engages said second portion.

4. The device according to claim 1 where said tubular means includes a hollow shaft and a mounting cylinder disposed about said hollow shaft, said mounting cylinder having a threaded outer surface and said inner surface of said collar being threaded for threaded movement over said threaded outer surface and the outer surface of said mounting cylinder and said inner surface of said collar are sized to form a gas tight seal.

5. A laparoscopic assembly for open laparoscopic surgery, said assembly providing a fluid tight conduit into a peritoneal cavity by insertion through an incision in a patient's abdomen, the assembly comprising:
   a cannula having tubular means for the introduction of surgical instruments into the body;
   a collar composed of a medically inert material, having a first portion having a generally conical outer surface diminishing in diameter from an upper end to a lower end, said outer surface of said first portion being deformable and resilient to conform to the contours of the skin surrounding the incision, a second portion integrally connected to and extending vertically from said upper end, a sealing flange integrally connected to an upper end of said second portion for forming a gas tight seal with a protruding lip on said cannula, said collar having an inner surface defining an axial passageway for acceptance of said tubular means;
   a tube engaged to said second portion and located intermediate said upper end of said collar and said sealing flange, a plurality of ears, each of said ears having notch means for receiving a suture, said ears operatively connected to said tube, whereby upon insertion of said cannula in the incision, said outer surface of said collar conforms to the skin surrounding the incision to create a fluid tight seal which can be maintained during movements of said cannula.

6. In open laparoscopic surgery, a method for creating a gas tight seal between a cannula and an incision in a patient's abdomen, said incision having contours and providing an opening into the patient's peritoneal cavity, comprising the steps of:
   assembling said cannula with a sleeve secured to a mounting cylinder of said cannula, said sleeve having a deformable and resilient outer surface;
   inserting a hollow shaft of said cannula through said incision and into said peritoneal cavity;
   inserting said sleeve into said incision and thereby establishing a conformance of said deformable and resilient outer surface of said sleeve to the contours of said incision, visually ascertaining said conformance, thereby creating a gas tight seal between said sleeve and said incision; and securing said sleeve to said patient's abdomen by attaching sutures to said abdomen and connecting said sutures to a rigid means on said sleeve while maintaining said gas tight seal between said sleeve and said incision.

7. The method as recited in claim 6, further comprising screwing said sleeve onto said mounting cylinder until a sealing flange on said sleeve abuts a positioning flange on said cannula, whereby a protruding lip on said positioning flange forces an outward radial displacement of said sealing flange to create a gas tight seal between said protruding lip and said sealing flange.

* * * * *

UNITED STATES PATENT AND TRADEMARK OFFICE
CERTIFICATE OF CORRECTION

PATENT NO. : 5,257,973
DATED : November 2, 1993
INVENTOR(S) : Raul Villasuso

It is certified that error appears in the above-indentified patent and that said Letters Patent is hereby corrected as shown below:

Column 4, line 49, "teflon" should be --polytetrafluorethylene--.

Signed and Sealed this

Fifteenth Day of November, 1994

Attest:

BRUCE LEHMAN

*Attesting Officer*     *Commissioner of Patents and Trademarks*